Sept. 28, 1965 C. KEEL ETAL Plant Pat. 2,556
REDBUD PLANT
Filed June 26, 1964
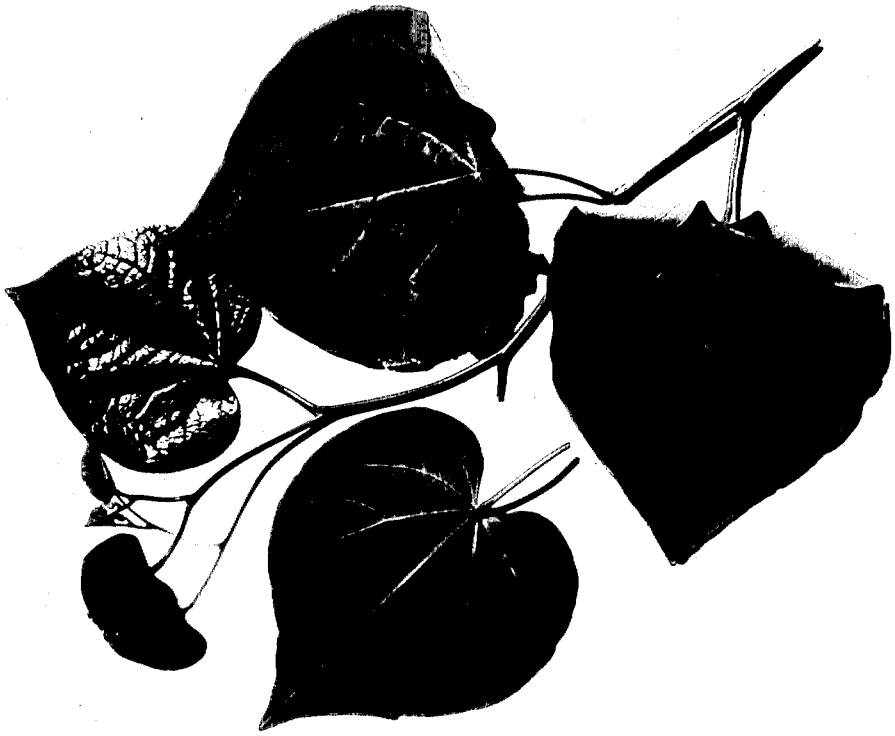
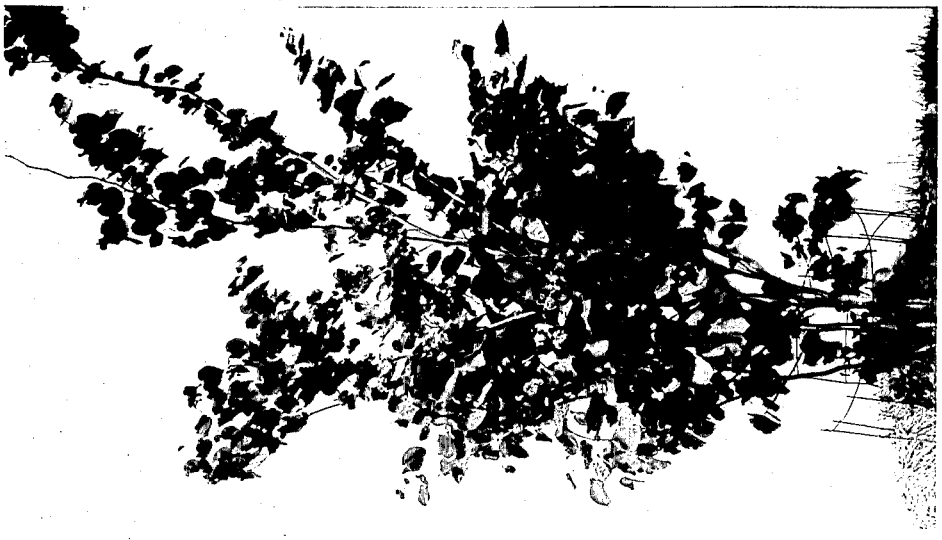
Inventors.
Charles Keel and
Eugene Hunley
By: Robert Cobb
Attorneys.

United States Patent Office

Plant Pat. 2,556
Patented Sept. 28, 1965

2,556
REDBUD PLANT

Charles Keel and Eugene Nunley, McMinnville, Tenn., assignors to Forest Nursery Co., Inc., McMinnville, Tenn., a corporation of Tennessee Filed June 26, 1964, Ser. No. 378,478
1 Claim. (Cl. Plt.—51)

The present invention relates to a new and distinct variety of redbud plant of the species botanically known as *Cercis canadensis,* which originated as an open-pollinated seedling discovered by us amongst a block of redbud plants of the regular *Cercis canadensis* species being grown under our direction and care in the nursery of our assignee at McMinnville, Tennessee.

Our attention was initially attracted to this new variety by its unusually attractive and distinctive brilliant Pansy Purple foliage which differed materially from the normal green-colored foliage of the other plants in the block, with the additional difference characterized by darker colored twigs, corresponding in color to Oxblood Red. Except for these principal differences, the new variety otherwise generally corresponded to the usual characteristics of the regular *Cercis canadensis* plants. Continued observations of the original seedling, as well as progeny thereof derived by budding, as performed by us in the nursery aforementioned at McMinnville, Tennessee, convinced us that they represented a new and distinct variety.

Asexual reproduction of our new variety by budding, as performed at McMinnville, Tennessee, shows that the foregoing characteristics and distinctions come true to form and are established and transmitted through succeeding propagations.

The accompanying drawing shows a typical specimen plant of our new redbud variety, together with typical specimens of the wood and foliage on a somewhat enlarged scale, as depicted in color as nearly true as it is reasonably possible to make the same in a color illustration of this character.

The following is a detailed description of our new variety, with color terminology in accordance with the Horticultural Colour Chart, issued by the British Colour Council in collaboration with the Royal Horticultural Society, except where general color terms of ordinary dictionary significance are obvious:

Locality where grown and observed: McMinnville, Tennessee.

*Plant*

Growth: Vigorous under good cultural conditions. Form—typical of common redbud, developing into a small tree with upright spreading branches.

Trunk: Smooth.

Branches: Smooth. Color—Oxblood Red.

Twigs: Slightly zig-zag form. Color—Purple Madder, Plate 1028, with whitish bloom, changing to Oxblood Red, Plate 00823/1, these colors darkening with age and becoming in the case of two-year-old twigs Garnet Brown, Plate 00918/2, with numerous, prominent, small, light tan lenticels.

Foliage:

*Leaves.* — Alternate; deciduous; simple; medium thickness; rounded cordate. Length—from 4 inches to 6 inches. Width—from 3½ inches to 6 inches. Margin—entire. Petiole—from 1½ inches to 2 inches. Color: New tip leaves—upper surface—shiny Garnet Lake, Plate 828; under surface—Garnet Lake, Plate 828/3. New mature leaves—upper surface—non-glossy Pansy Purple, Plate 928, with prominent veins showing a green coloration; lower surface—Pansy Purple, Plate 928/3, with veins of same color and petioles being Pansy Purple, Plate 928. Mature summer leaves—upper surface—Spinach Green, Plate 0960/1, with fusing of light Pansy Purple still prominent, especially in center and lower portion of leaf and with prominent veins of light green color; lower surface—Willow Green, Plate 000862/1, with fusing of very light Pansy Purple, and petioles showing a blending of Garnet Brown, Plate 00918 and Pansy Purple, Plate 928.

*Flowers*

Flowers: Sparse; appear before the leaves; pea-shaped; borne in clusters.

*Size.*—Same as *Cercis canadensis.*

*Color.*—Rosy magenta.

*Fruit*

Fruit: Linear-oblong; legume; from 2 inches to 3 inches long.

*General observations*

Disease and insect resistance: Comparable to that of common *Cercis canadensis,* as determined by comparison therewith when grown under the same field conditions at McMinnville, Tennessee.

Hardiness: Very good; has withstood temperature conditions as low as minus 14° F. without damage, even without special protection, as occurred in the nursery aforementioned at McMinnville, Tennessee.

We claim:

A new and distinct variety of redbud plant, substantially as herein shown and described, characterized particularly as to novelty by its distinctive and attractive brilliant Pansy Purple foliage, with twigs of Oxblood Red color.

No references cited.

ABRAHAM G. STONE, *Primary Examiner.*